United States Patent [19]

Pang et al.

[11] Patent Number: 5,929,093
[45] Date of Patent: Jul. 27, 1999

[54] BIFUNCTIONAL ACETYLCHOLINESTERASE REACTIVATORS

[75] Inventors: Yuan-Ping Pang, Ponte Vedra Beach, Fla.; Stephen Brimijoin, Rochester, Minn.

[73] Assignee: Mayo Foundation for Medical Education and Research, Rochester, Minn.

[21] Appl. No.: 08/873,794

[22] Filed: Jun. 12, 1997

Related U.S. Application Data

[60] Provisional application No. 60/019,461, Jun. 13, 1996.

[51] Int. Cl.$^6$ .......................... A01N 43/40; C07D 401/00
[52] U.S. Cl. ......................... 514/332; 514/333; 546/256
[58] Field of Search ........................ 546/113–134, 256; 514/332, 333

[56] References Cited

U.S. PATENT DOCUMENTS

| | | | |
|---|---|---|---|
| 4,631,286 | 12/1986 | Shutske et al. | 514/297 |
| 4,816,456 | 3/1989 | Summers | 514/255 |
| 4,868,177 | 9/1989 | Shutske et al. | 514/228.2 |
| 5,026,897 | 6/1991 | Chiang et al. | 560/58 |
| 5,391,553 | 2/1995 | Shutske et al. | 514/290 |

FOREIGN PATENT DOCUMENTS

| | | |
|---|---|---|
| 2264707 | 9/1993 | United Kingdom . |
| WO89/02739 | 4/1989 | WIPO . |

OTHER PUBLICATIONS

Bindra, J.S., et al., "Synthesis, Pharmacological Activities & Physico–chemical Properties of 4–(Substituted amino/N4–arylpiperazinyl/aminocarbonyl)–2,3–polymethylene-quinolines", *Indian Journal of Chemistry*, vol. 26B, pp. 318–329, (Apr. 1987).

Chen, T.K., et al., "Diacridines, Bifunctional INtercalators. Chemistry and Antitumor Activity", *J. Med. Chem.*, 21, 868–874, (1978).

Davis, K.L., et al., "Tacrine", *The Lancet, 345*, 625–630, (1995).

Fleisher, J.H., et al., "Reactivation by pyridinium aldoxine methochloride (PAM) of inhibited cholinesterase activity in dogs after poisoning with pinacolyl methylphosphonofluo-ridate (SOMAN)", *J. of Pharmaco. and Exper. Ther.*, 156, 345–351, (1967).

Galanakis, D., et al., "Synthesis and Structure—Activity Relationships of DeQualinium Analogues as K+ Channel Blockers. Investigations on the Role of the Charged Het-erocycle", *J. Med. Chem., 38*, 595–606, (1995).

Himel, C.M., et al., "Acidine Araphanes: A New Class of Probe Molecules for Biological Systems", *Science*, 205, 1277–1279, (1979).

Hobbiger, F., et al., "New Potent Reactivators of Acetocho-linesterase Inhibited by Tetraethyl Pyrophosphate", *Nature*, 182, 1498–1499, (1958).

Hobbiger, F., et al., "Protection by Oximes of bis–Pyri-dinium Ions Against Lethal Diisopropyl Phosphonofluori-date Poisoning", *Nature, 182,* 1672–1673, (1958).

Hobbinger, F., "Reactivation of Phosphorylated Acetylcho-linesterase, Chapter 21", *Handbook of Experimental Pharmacology*, Series title "Cholinesterase and Anticholinest-erase agents", G.B. Koelle, ed., Springer, pub., 921–988, (1963).

Joshi, H.C., et al., "Preparation of Bisquaternary Pyridinium Aldoximes", *Indian J. of Chem.*, 17B, 2, 162–163, (1979).

Nelson, M.E., et al., "9–Aminoacridines Act at a Site Different from that for Mg2+ in Blockade of the N-Meth-yl–D–Aspartate Receptor Channel", *Mol. Pharmacol.*, 46, 151–160, (1994).

Pang, Y., et al., "Highly Potent, Selective, and Low Cost Bis–tetrahydroaminacrine Inhibitors of Acetylcholinest-erase", *The Journal of Biological Chemistry*, vol. 271, No. 39, pp. 23646–23649, (Sep. 27, 1996).

Patocka, J., et al., "Kinetics of Inhibition of Cholinesterases by 1,2,3,4–Tetra–Hydro–9–Aminoacridine in vitro", *Collect. Czech. Chem. Commun.*, 41, 816–824, (1976).

Poziomek, E.J., et al., "Pyridinium Aldoximes", *J. of Org. Chem. Soc., 23,* 714–717, (1957).

Rastogi, S.N., et al., "Local Anaesthetic Activity of 9–Alky-lamino–1,2,3,4–Tetrahydroacridines: Structure–Activity Relationship Study", *Indian Journal of Pharmacology*, 19, pp. 44–48, (1987).

Steinberg, G.M., et al., "A Hydrophobic Binding Site in Acetylcholinesterase", *Journal of Medinicinal Chemistry*, vol. 18, No. 11, pp. 1056–1061, (May 12, 1975).

Taylor, J.L., et al., "Conformers of Acetylcholinesterase: A Mechanism of Allosteric Control", *Mol. Pharmacol.*, 45, 74–83, (1994).

Wilson, I.B., et al., "A Power Reactivator of Alkylphos-phate–Inhibited Acetylcholinesterase", *Biochim. Biophys. Acta*, 18, 168–170, (1955).

Broomfield et al., Binding of soman antidotes to ACh receptors, Biochem. Pharmacol., 1987, 36(7)1017–22.

Inns et al., The efficacy of bispyridinium derivatives, J. Pharm. Pharamcol., 35(7), 427–33, 1983.

(List continued on next page.)

*Primary Examiner*—Jose' G. Dees
*Assistant Examiner*—Alton Pryor
*Attorney, Agent, or Firm*—Schwegman, Lundberg, Woessner & Kluth, P.A.

[57] ABSTRACT

Compounds of formula I:

$$Ar^1 - R^1 - Ar^2 \qquad (I)$$

wherein $Ar^1$, $Ar^2$, and $R^1$ have any of the values defined in the specification, and their pharmaceutically acceptable salts, are acetylcholinesterase (AChE) reactivators useful as antidotes for organophosphate poisoning in mammals. Also disclosed are pharmaceutical compositions, processes for preparing compounds of formula (I), methods for the use of compounds of formula (I), and intermediates for the preparation thereof.

19 Claims, 3 Drawing Sheets

OTHER PUBLICATIONS

Taylor et al., Interaction of fluorescene probes with AChE, Biochemistry, 14(9), 1989–97, 1975.

Patocka et al., Affinity of bis–quaternary pyridinedialdoximes for the active center, Collect. Czech. Chem. Commun., 37(6), 2110–16, 1972.

Greenspan et al., Effect of fluoride on the rxns of methanesulfonates, Mol. Pharmacol., 6(5), 460–67, 1970.

Raftery et al., Biochemical studies on T. californica ACh receptors, J. Supramolecular Struct., 1(4–5), 360–67, 1973.

Oldiges et al, Antidote studies against phosphate, Beispiele Angew. Forsch., Fraunhofer–Ges. Foerder. Angew. Forsch., 1970–1971, 119–22, 1971.

Berry, W.K., et al., "Oximes of AW–Diquarternary Alkane Salts as Antidotes to Organophosphate Anticholinesterases", *British Journal of Pharmacology and Chemotherapy,* (*14*), 186–191, (1959).

Clement, J.G., "Efficacy of Various Oximes Against GF (cyclohexyl mehtylphosphonofluoridate) Poisoning Mice", *Archives of Toxicology* (66), 143–144, (1992).

de Jong, L.P., et al., "Stereospecific Reactivation by Some Hagedorn–Oximes of Acetylcholinesteras From Various Species Including Man, Inhibiting by Soman", *Biochemical Pharmacology,* (33), 1119–1125, (Apr. 1, 1984).

Hamilton, M.G., et al., "HI–6 Therapy of Soman and Tabun Poisoning in Primates and Rodents", *Archives of Technology* (63), 144–149, (1989).

Hobbiger, F., et al., "New Potent Reactivators of Acetochoilinesterase Inhibited by Tetraethyl PyroPhosphate", *Nature* (182), 1498–1499, (Oct. 4, 1958).

Hobbiger, F., et al., "Protection Against Lethal Oraganophosphate Poisoning By Quarternary Pyridine Aldoximes", *British Journal of Pharmocology and Chemotherapy,* (14), 192–201, (1959).

Hobbiger, F., et al., "Reactivation of Phosphorylated Acetocholinesterases by Pyridinium Aldoximes and Related Compounds", *Biochemical Journal,* (75), 363–372, (1960).

Korte, W.D., et al., "Degradation of Three Related Bis(pyridinium)aldoximes in Aqueous Solutions at High Concentrations: Examples of Unexpectedly Rapid Amide Group Hydrolysis", *Journal of Pharmeceutical Sciences* (82), 782–786, (Aug. 1993).

Kusic, R., et al., "HI–6 in Man: Blood Levels, Urinary Secretion, and Tolerance after IntraMuscular Administration of Oxime to Healthy Volunteers", *Fundamental and Applied Toxicology* (5), S89–S97, (Dec. 1985).

Lundy, P.M., et al., "Comparison of Several Oximes Against Poisoning by Soman, Tabun and GF", *Toxicology* (72), 99–105, (1992).

Oldiges, H., et al., "Pyridinium und Imidazolimsalze als Antidote Gegenuber Soman und Paraoxonvergiftungen Bei Mausen", *Archiv fur Toxikologie* (26), 293–305, (1970).

Scaife, J.F., "Oxime Reactivation Studies of Inhibited True and Pseudo Cholinesterase", *Canadian Journal of Biochemistry and Physiology,* 1301–1311, (Jul. 1959).

Williams, J.F., "Optimization Strategies for the Polymerase Chain Reaction", *Biotechniques* (7), 762–768, (Jul./Aug. 1989).

Wilson, I.B., et al., "Reactivation of Alkylphosphate Inhibited Acetylcholinesterase by BIS Quaternary Derivatives of 2–PAM and 4–PAM", *Biochemical Pharmacology,* (1), 200–206, (1958).

Wolthius, O.L., et al., "Successful Oxime Therapy One Hour after Soman Intoxication in the Rat", *European Journal of Pharmacology* (*49*), 415–425, (Jun. 15, 1978).

BIFUNCTIONAL ACETYLCHOLINESTERASE REACTIVATORS

PRIORITY OF INVENTION

This application claims priority under 35 U.S.C. §119 (e) from U.S. Provisional Patent Application No. 60/019,461, filed on Jun. 13, 1996, which is hereby incorporated herein by reference.

BACKGROUND OF THE INVENTION

Organophosphorous compounds are used in chemical weapons, including nerve agents such as methylphosphonofluoridic acid 1-methyl-ethyl ester (sarin), pinacolyl methylphosphono fluoridate (soman), and methylphosphonothioic acid S-[2-[bis(1-methylethyl)amino]ethyl]O-ethyl ester (VX), and in insecticides such as phosphoric acid diethyl 4-nitrophenyl ester (paraoxon), diethyl-p-nitrophenyl monothiophosphate (parathion) and phosphorothioic acid O-(3-chloro-4-methyl-2-oxo-2H-1-benzopyran-7-yl) O,O-diethyl ester (coumaphos). Exposure to even small amounts of a nerve agent can be fatal. In humans, the mechanism of organophosphate poisoning involves reaction with a serine hydroxyl group in the active site of a key enzyme acetylcholinesterase ("AChE") producing an inactive and phosphorylated enzyme. The classical therapeutic approach for reactivating an inactive phosphorylated enzyme is treatment with nucleophilic oximes, which react with phosphorylated AChE and release the active enzyme. See I. B. Wilson; S. A. Ginsburg Biochem. Biophys. Acta, 1955, 18, 168–170.

Oximes such as pyridinium aldoxime methochloride ("PAM") have been used to treat the actions of some organophosphates, however, they are not effective for other organophosphates such as soman (J. H. Fleisher et al. J. Pharmacol. Exp. Ther. 1967, 156, 345–351). Derivatives of 1-methylpyridinium-aldoxime iodides have also been used as reactivators of AChE (E. J. Poziomek et al. J. Org. Chem. 1958, 23, 714–717). Such oximes are structurally analogous to the AChE inhibitor 9-amino-1,2,3,4-tetrahydroacridine ("THA"), which has been shown to bind to both a catalytic binding site and a peripheral binding site of AChE (See FIG. 2) (Y.-P. Pang et al. J. Biol. Chem. 1996, 271, 23646–23649).

The effectiveness of an oxime AChE reactivator depends on the intrinsic equilibrium constant for the equilibrium illustrated in FIG. 1. Reactivation is effective only when enzyme dephosphorylation is faster than oxime dephosphorylation. There is currently a need for effective reactivators of AChE.

SUMMARY OF THE INVENTION

The invention comprises novel compounds which are AChE reactivators, useful as antidotes for organophosphate poisoning. According to the invention there is provided a compound of the invention which is a compound of formula I:

$$Ar^1—R^1—Ar^2 \quad (I)$$

wherein $Ar^1$ and $Ar^2$ are each independently (a) a monocyclic heteroaromatic ring containing five or six ring atoms, attached to $R^1$ via a ring nitrogen, wherein said ring optionally comprises one, two or three additional heteroatoms, each independently selected from the group consisting of non-peroxide oxygen, sulfur, and N(X); (b) a benz- or benzo-derivative of said ring; or (c) an ortho-fused bicyclic heterocycle comprising a propylene, trimethylene, or tetramethylene diradical fused to said heteroaromatic ring; wherein $Ar^1$ and $Ar^2$ are each substituted on a ring carbon atom with a radical of formula —CHNOH; and $Ar^1$ and $Ar^2$ are optionally substituted with one, two, or three additional substituents selected from the group consisting of $(C_1-C_6)$ alkyl, $(C_1-C_6)$alkoxy, phenyl, and benzyl;

X is absent or is H,O,$(C_1-C_4)$alkyl, phenyl or benzyl; and $R^1$ is an unbranched $(C_7)$-, $(C_8)$-, or $(C_9)$alkylene chain, optionally substituted with one, two, or three substituents selected from the group consisting of $(C_1-C_3)$alkoxy, hydroxy, oxo, and halo; or $R^1$ is an unbranched $(C_2-C_{10})$alkylene chain comprising at least one, i.e. 1, 2, or 3, divalent radicals selected from the group consisting of —OC(=O)—, —NHC(=O)—, —NHC(=O)C(=O)NH—, —OCH$_2$C=CCH$_2$O—, 1,4-phenylene, 1,3-phenylene, 1,2-phenylene, 1,4-cyclohexadiyl, 1,3-cyclohexadiyl, and 1,3-cyclopentadiyl; or a pharmaceutically acceptable salt thereof.

Compounds of the invention have activity as reactivators of AChE, and therefore may be useful to counter or attenuate the toxic effects of chemical agents which act on the cholinergic system. Accordingly, the invention includes a method comprising attenuating the effects on a mammal caused by exposure to a chemical agent that covalently inhibits AChE, by administering to said mammal (such as for example a human) an effective amount of a compound of formula I; or a pharmaceutically acceptable salt thereof. The compound may be administered either prior to exposure or after exposure to said chemical agent.

Compounds of the invention may also be useful to counter or attenuate the toxic effects of chemical agents which act on the cholinergic system when administered in combination with atropine (Poziomek et al. J. Org. Chem. 1958, 23, 714–717) and/or other antimuscarinic or antinicotinic agents such as carbaphens (U.S. Pat. No. 5,026,897). Accordingly, the invention includes a method comprising attenuating the effects on a mammal caused by exposure to a chemical agent that covalently inhibits AChE, by administering to said mammal (such as for example a human) an effective amount of a compound of formula I; or a pharmaceutically acceptable salt thereof, in combination with atropine and/or another antimuscarinic or antinicotinic agent. Compounds of the invention may be administered with said antimuscarinic or said antinicotinic agent simultaneously as a single dose, simultaneously in individual doses, or sequentially; each therapeutic agent may be administered prior to exposure or after exposure to said chemical agent.

DETAILED DESCRIPTION OF THE INVENTION

Figure 1:
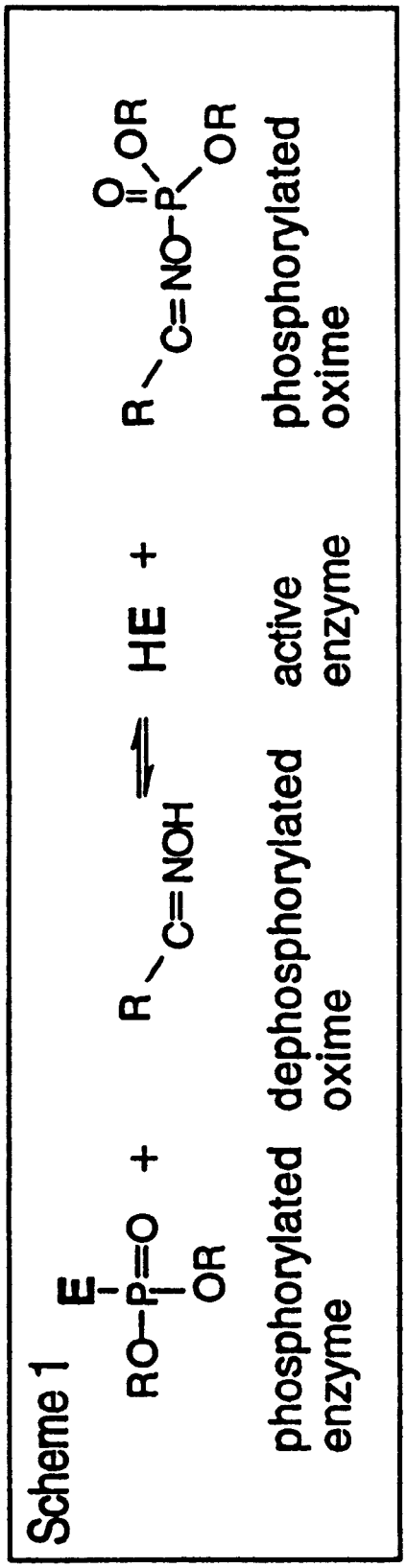
FIG. 1 shows the equilibrium equation for oxime reactivation of AChE.
Figure 2:
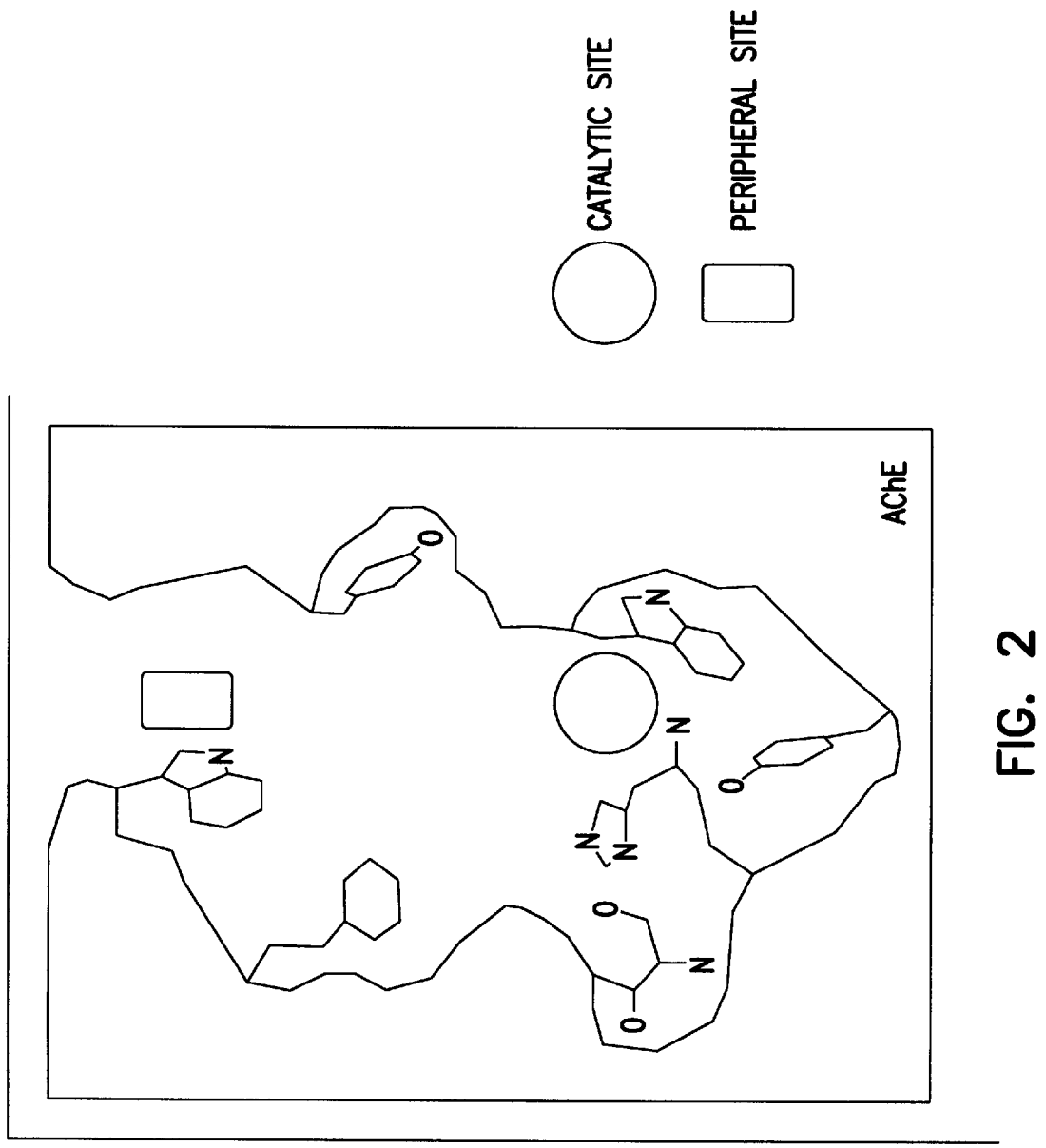
FIG. 2 shows the catalytic and peripheral binding sites of AChE.

In the following detailed description, reference is made to the accompanying figures which from a part hereof, wherein specific embodiments of the invention may be illustrated. It is to be understood that other embodiments may be utilized and structural changes may be made without departing from the scope of the present invention.

The following definitions are used, unless otherwise described: halo is fluoro, chloro, bromo, or iodo. Alkyl, and alkoxy denote both straight and branched groups; but reference to an individual radical such as "propyl" embraces only the straight chain radical, a branched chain isomer such as "isopropyl" being specifically referred to.

It will be appreciated by those skilled in the art that compounds of the invention having a chiral center may exist in and be isolated in optically active and racemic forms. Some compounds may exhibit polymorphism. It is to be understood that the present invention encompasses any racemic, optically-active, polymorphic, or stereoisomeric form, or mixtures thereof, of a compound of the invention, which possess the useful properties described herein, it being well known in the art how to prepare optically active forms (for example, by resolution of the racemic form by recrystallization techniques, by synthesis, from optically-active starting materials, by chiral synthesis, or by chromatographic separation using a chiral stationary phase) and how to determine AChE reactivating activity using the tests described herein, or using tests which are well known in the art.

Specific values listed below for radicals, substituents, and ranges, are for illustration only and they do not exclude other defined values or other values within defined ranges for the radicals and substituents.

Specifically, $(C_1-C_6)$alkyl can be methyl, ethyl, propyl, isopropyl, butyl, iso-butyl, sec-butyl, pentyl, 3-pentyl, or hexyl; $(C_1-C_4)$alkyl can be methyl, ethyl, propyl, isopropyl, butyl, iso-butyl, or sec-butyl; $(C_1-C_6)$alkoxy can be methoxy, ethoxy, propoxy, isopropoxy, butoxy, iso-butoxy, sec-butoxy, pentoxy, 3-pentoxy, or hexoxy; and $(C_1-C_3)$alkoxy can be methoxy, ethoxy, propoxy, or isopropoxy;

Specifically, $Ar^1$ and $Ar^2$ can each independently be 4-hydroxyiminomethyl-1-pyridyl, 3-hydroxyiminomethyl-1-pyridyl, 2-hydroxyiminomethyl-1-pyridyl, 2-hydroxyiminomethyl-1-methyl-3-imidazolyl, 4-hydroxyiminomethyl-1quinolyl, 3-hydroxyiminomethyl-1-quinolyl, or 2-hydroxyiminomethyl-1-quinolyl.

Specifically, X can be absent, or is hydrogen or methyl.

A specific value for $R^1$ is an unbranched $(C_7)$-, $(C_8)$-, or $(C_9)$alkylene chain, optionally substituted with one, two, or three substituents selected from the group consisting of $(C_1-C_3)$alkoxy, hydroxy, oxo, and halo.

A specific value for $R^1$ is an unbranched $(C_2-C_{10})$ alkylene chain comprising within said chain a divalent radical selected from the group consisting of —OC(=O)—, —NHC(=O)—, —NHC(=O)C(=O)NH—, and —OCH$_2$C=CCH$_2$O—.

A specific value for $R^1$ is an unbranched $(C_2)$-, $(C_3)$-, $(C_4)$-, or $(C_5)$-alkylene chain comprising within said chain a divalent radical selected from the group consisting of 1,4-phenylene, 1,3-phenylene, 1,2-phenylene, 1,4-cyclohexadiyl, 1,3-cyclohexadiyl, and 1,3-cyclopentadiyl.

A specific value for $R_1$ is 1,7-heptadiyl—(CH$_2$)$_7$—, 1,8-octadiyl —(CH$_2$)$_8$— or 1,9-nonadiyl —(CH$_2$)$_9$—.

A more specific value for $R^1$ is an unbranched $(C_6)$-, $(C_7)$-, $(C_8)$-, $(C_9)$-, or $(C_{10})$-alkylene chain comprising within said chain a divalent radical —OC(=O)—or —NHC(=O)—.

A more specific value for $R^1$ is an unbranched $(C_2)$-, $(C_3)$-, $(C_4)$-, or $(C_5)$-alkylene chain comprising within said chain a divalent radical —NHC(=O)C(=O)NH— or —OCH$_2$C=CCH$_2$O—.

A more specific value for $R^1$ is 1,7-heptadiyl —(CH$_2$)$_7$—, or 1,8-octadiyl —(CH$_2$)$_8$—.

A specific group of compounds are compounds of formula I wherein: $Ar^1$ and $Ar^2$ are each independently 4-hydroxyiminomethyl-1-pyridyl, 2-hydroxyiminomethyl-1-pyridyl, 2-hydroxyiminomethyl-1-methyl-3-imidazolyl, 4-hydroxyiminomethyl-1-quinolyl, 3-hydroxyiminomethyl-1-quinolyl, or 2-hydroxyiminomethyl-11-quinolyl.

A specific group of compounds are compounds of formula I wherein $Ar^1$ and $Ar^2$ are the same.

A specific group of compounds are compounds of formula I wherein $Ar^1$ and $Ar^2$ are different.

A more specific group of compounds are compounds of formula I wherein: $Ar^1$ and Ar2 are the same, and are selected from the group consisting of 4-hydroxyiminomethyl-1-pyridyl, 2-hydroxyiminomethyl-1-methyl-3-imidazolyl, 4-hydroxyiminomethyl-1-quinolyl, 3-hydroxyiminomethyl-1-quinolyl, and 2-hydroxyiminomethyl-1-quinolyl.

A preferred value for $R^1$ is an unbranched $(C_7)$alkylene chain, optionally substituted with one, two or three substituents selected from the group consisting of $(C_1-C_3)$alkoxy, hydroxy, oxo, and halo.

A more preferred value for $R^1$ is 1,7-heptadiyl—(CH$_2$)$_7$—.

Compounds of the invention thus possess two oxime groups linked by an alkylene chain, which permits binding at the peripheral and catalytic AChE binding sites. Binding of one oxime at the peripheral site increases the effective concentration of the other oxime in the catalytic site as described by Koshland's "proximity and orientation effect" (Koshland, D. E. (1962) *J, Theo. Biol.* 2, 75–86). An increase in the effective concentration of oxime causes the equilibrium equation in FIG. 1 to shift in favor of AE and phosphorylated oxime. In addition, following enzyme reactivation, the phosphorylated bis-oxime becomes too bulky to remain at AChE's catalytic site, so the effective concentration of phosphorylated oxime decreases, and further shifts the equilibrium toward AE.

Processes for preparing compounds of formula I are provided as further embodiments of the invention and are illustrated by the following procedures in which the meanings of the generic radicals are as given above unless otherwise qualified.

Compounds of formula I wherein $Ar^1$ and $Ar^2$ are the same can be prepared by alkylating the requisite heterocyclic amine with a compound of formula Y—$R^1$—Z wherein Y and Z are each a suitable leaving group. Solvents, and reaction conditions suitable for alkylating aromatic amines are well known in the art. For example, the alkylation may conveniently be carried out under conditions similar to those described in Example 1 or Example 9. Suitable leaving groups Y and Z may be selected from leaving groups which are well known in the art, such as for example, chloro, bromo, iodo, triflate, mesylate, or tosylate.

Compounds of formula I wherein $Ar^1$ and $Ar^2$ are not the same can be prepared by alkylating the requisite heterocyclic amine $Ar^1$H with a compound of formula Y—$R^1$—Z wherein Y and Z are each a suitable leaving group. The resulting product having one group $Ar^1$, can subsequently be used to alkylate a second heterocyclic amine $Ar^2$H to give the desired product.

For compounds of the invention which comprise negatively charged counterions, such counterions may be exchanged for other counterions using procedures which are well known in the art. For example, the exchange may conveniently be carried out using an ion exchange resin as described in Example 9.

A protecting group may optionally be used while performing the above described procedures; the protecting group may be removed at a convenient time during a procedure, or may be removed when the final compound is to be formed.

If not commercially available, the necessary starting materials of formula $Ar^1H$, $Ar^2H$ or $Y—R^1—Z$ to carry out the above procedures may be made by procedures which are well known in the art.

Examples of pharmaceutically acceptable salts are organic acid addition salts formed with acids which form a physiological acceptable anion, for example, tosylate, methanesulfonate, acetate, citrate, malonate, tartarate, succinate, benzoate, ascorbate, α-ketoglutarate, and (α-glycerophosphate. Suitable inorganic salts may also be formed, including hydrochloride, sulfate, nitrate, bicarbonate, and carbonate salts.

Pharmaceutically acceptable salts may be obtained using standard procedures well known in the art, for example by reacting a sufficiently basic compound such as an amine with a suitable acid affording a physiologically acceptable anion.

The compounds of formula I can be formulated as pharmaceutical compositions and administered to a mammalian host, such as a human patient in a variety of forms adapted to the chosen route of administration, i.e., orally or parenterally, by intravenous, intramuscular, topical or subcutaneous routes.

Thus, the present compounds may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form must be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the present compounds may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions which can be used to deliver the compounds of formula I to the skin are disclosed in Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508).

Useful dosages of the compounds of formula I can be determined by comparing their in vitro activity, and in vivo activity in animal models. Methods for the extrapolation of effective dosages in mice, and other animals, to humans are known to the art; for example, see U.S. Pat. No. 4,938,949.

Generally, the concentration of the compound(s) of formula I in a liquid composition, such as a lotion, will be from about 0.1–25 wt-%, preferably from about 0.5–10 wt-%. The concentration in a semi-solid or solid composition such as a gel or a powder will be about 0.1–5 wt-%, preferably about 0.5–2.5 wt-%. Single dosages for injection, inhalation, infusion or ingestion will generally vary between 50–1500 mg, and may be administered, i.e., 1–3 times daily, to yield levels of about 0.5–50 mg/kg, for adults.

Accordingly, the invention includes a pharmaceutical composition comprising a compound of formula I as described hereinabove; or a pharmaceutically acceptable salt thereof; and a pharmaceutically acceptable diluent or carrier.

Biological Activity

The AChE reactivating activity of compounds of the invention can be demonstrated in a reactivation assay using human red blood cell AChE inhibited by exposure to the organophosphate anticholinesterase drug, echothiophate, at a concentration of $10^{-7}$ M. When added for 1 hour at a concentration of $10^{-6}$ M, all compounds of the invention which were tested produced AChE reactivation.

Compounds of the invention wherein $Ar^1$ and $Ar^2$ were both 3-hydroxyiminomethyl-1-pyridyl (Compounds 2b–2d) gave 12–15% reactivation. The standard drug, 2-pralidoxime (2-PAM) gave 17% reactivation. As shown in Table 1 and Table 2, compounds of the invention wherein $Ar^1$ and $Ar^2$ were both 2-hydroxyiminomethyl-1-pyridyl (3b–3d) and compounds of the invention wherein $Ar^1$ and $Ar^2$ were both 4-hydroxyiminomethyl-1-pyridyl (1b–1d) were more effective, demonstrating up to 80% and 61% reactivations, respectively. At higher concentrations, compounds 1b–1d and 3b–3d produced 100% reactivation.

In addition, full dose-response curves for compound 1b showed it to be ten-fold more potent in reactivation than 2-PAM.

TABLE 1

Percentages of AChE reactivation by 2-pralidoxime (2-PAM) and compounds 3a–3d tested in single concentrations of $10^{-6}$ M; values are means ± standard errors of 4 measurements.

| Compound | 2-PAM | 3a | 3b | 3c | 3d |
|---|---|---|---|---|---|
| Reactivation | 17 ± 2.8 | 67 ± 0.8 | 80 ± 3.7 | 69 ± 4.7 | 58 ± 0.5 |

TABLE 2

Percentages of AChE reactivation by 2-pralidoxime (2-PAM) and compounds 1a–1d tested in single concentrations of $10^{-6}$ M; values are means ± standard errors of 4 measurements.

| Compound | 2-PAM | 1a | 1b | 1c | 1d |
|---|---|---|---|---|---|
| Reactivation | 17 ± 2.8 | 47 ± 1.8 | 61 ± 3.2 | 44 ± 1.7 | 31 ± 2.3 |

Compounds linked with a heptylene linker ($R^1$=1,7-heptadiyl) demonstrated the highest reactivation for compounds of the invention wherein $Ar^1$ and $Ar^2$ were both 2-hydroxyiminomethyl-1-pyridyl and for compounds of the invention wherein $Ar^1$ and $Ar^2$ were both 4-hydroxyiminomethyl-1-pyridyl. This activity-chain length relationship agrees with the finding that a heptylene linker amply bridges the distance of 18 Å between the catalytic and peripheral AChE binding sites (Y.-P. Pang et al. *J. Biol. Chem.* 1996, 271, 23646–23649). Preferred compounds of the invention comprise two oxime groups separated by 14–20 Å and more preferably by 16–18 Å. One skilled in the art can readily identify such preferred compounds of the invention using known chemical bond lengths and angles, or using computer based chemical modeling programs which are well known in the art.

The invention will now be illustrated by the following non-limiting examples wherein unless otherwise stated:

a) Synthetic intermediates were purchased from Aldrich Chemical Co. (Milwaukee, Wis.) and were used as received;

b) Reagents and solvents were purchased as reagent grade and used without further purification;

c) Air-sensitive reactions were carried out under nitrogen;

d) Yields were not optimized;

e) Melting points were determined on a Gallenkamp capillary melting point apparatus and are uncorrected;

f) $^1$H NMR spectra were recorded on a Bruker AC-300 Spectrometer; and g) Mass spectra were aquired on a Finnigan MAT-900 Spectrometer.

EXAMPLES

Example 1

Figure 3:
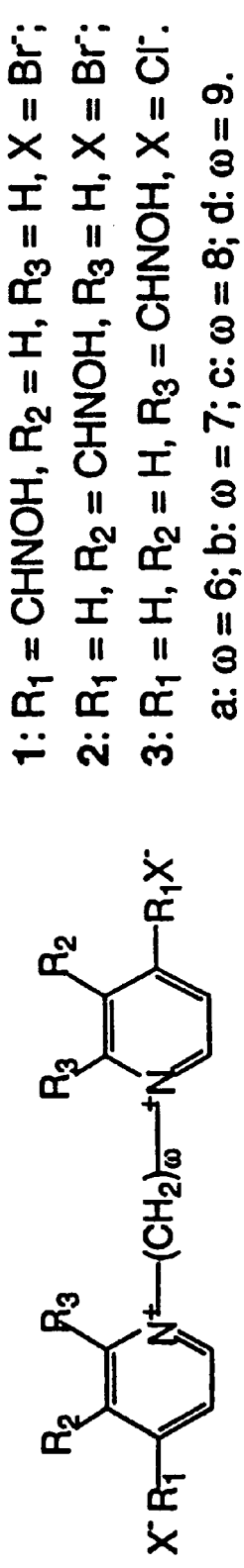
FIG. 3 shows compounds exemplified herein.

1,7-Heptylene-bis-N,N'-4-pyridiniumaldoxime dibromide (FIG. 3, 1b).

4-Pyridinealdoxime (2.8 g, 23.4 mmol) and 1,7-dibromoheptane (2.0 g, 7.8 mmol) were added to 30 ml of absolute ethanol. The reaction mixture was refluxed for 48 hours and cooled to room temperature. The resulting solid was collected by filtration and dried under vacuum to give the title compound; yield: 85%; m.p. 206.2–207.5 (dec); IR (KBr): 3449, 3021, 1642, 1583, 1518, 1462, 1429, 1294, 1003, 833, 735 and 546 cm$^{-1}$; $^1$H-NMR (300 MHz, DMSO-d$_6$): d 12.83 (s, 2H), 9.08 (d, J=6.48 Hz, 4H), 8.44 (s, 2H), 8.24 (d, J=6.57 Hz, 4H), 4.58 (t,J=7.1 Hz, 4H), 2.01–1.81 (m, 4H) and 1.41–1.21 (m, 6H); $^{13}$C-NMR (75.46 MHz, DMSO-d$_6$): d 148.3, 145.1, 144.9, 124.0, 60.2, 30.4, 27.7 and 25.1; MS (ESI) m/z: 423 (M-Br$^-$), 421 (M-Br$^-$). HRMS found for C$_{19}$H$_{26}$BrN$_4$O$_2$: 423.1206, 421.1245, calculated for C$_{19}$H$_{26}$BrN$_4$O$_2$: 423.1221, 421.1239.

Example 2

1,6-Hexylene-bis-N,N'-4-pyridiniumaldoxime dibromide (FIG. 3, 1a).

Using a procedure similar to that described in Example 1, except replacing the 1,7-dibromoheptane used therein, with 1,6-dibromohexane, the title compound was prepared; yield: 87%; m.p. 231.4–232.9 (dec.); IR (KBr): 3483, 3090, 2972, 2853, 2724, 1641, 1610, 1452, 1296 1174, 997, 922, 837 and 736 cm$^{-1}$; $^1$H-NMR (300 MHz, DMSO-d$_6$): d 12.83 (s, 2H), 9.15 (d, J=5.82 Hz, 4H), 8.46 (s, 2H), 8.26 (d, J=6.6 Hz, 4H), 4.62 (t, J=7.17 Hz, 4H), 2.03–1.83 (m, 4H) and 1.44–1.24 (m, 4H); $^{13}$C-NMR (75.46 MHz, DMSO-d$_6$): d 148.3, 145.1, 145.0, 124.0, 60.0, 30.2 and 24.6; MS (ESI) m/z: 409 (M–Br⁻), 407 (M–Br⁻). HRMS found for $C_{18}H_{24}BrN_4O_2$: 409.1070, 407.1100, calculated for $C_{18}H_{24}BrN_4O_2$: 409.1064, 407.1082.

Example 3

1,8-Octylene-bis-N,N'-4-pyridiniumaldoxime dibromide (FIG. 3, 1c).

Using a procedure similar to that described in Example 1, except replacing the 1,7-dibromoheptane used therein, with 1,8-dibromooctane, the title compound was prepared; yield: 74%; m.p. 224.5–226.2 (dec.); IR (KBr): 3225, 3065, 2897, 2712, 1984, 1658, 1602, 1514, 1425, 1292, 1174, 1098, 987, 845, 729 and 550 cm⁻¹; ¹H-NMR (300 MHz, DMSO-$d_6$): d 12.82 (s, 2H), 9.11 (d, J=6.48 Hz, 4H), 8.46 (s, 2H), 8.25 (d, J=6.6 Hz, 4H), 4.60 (t, J=7.1 Hz, 4H), 2.01–1.81 (m, 4H), 1.40–1.20 (m, 8H); ¹³C-NMR (75.46 MHz, DMSO-$d_6$): d 148.3, 145.1, 144.9, 124.0, 60.1, 30.5, 28.1 and 25.2; MS (ESI) m/z: 437 (M–Br⁻), 435 (M–Br⁻). HRMS found for $C_{20}H_{28}BrN_4O_2$: 437.1376, 435.1412, calculated for $C_{20}H_{28}BrN_4O_2$: 437.1378, 435.1395.

Example 4

1,9-Nonylene-bis-N,N'-4-pyridiniumaldoxime dibromide (FIG. 3, 1d).

Using a procedure similar to that described in Example 1, except replacing the 1,7-dibromoheptane used therein, with 1,9-dibromononane, the title compound was prepared; Yield: 74%; m.p. 176.2–178.1 (dec.); IR (KBr): 3483, 3113, 2716, 1641, 1608, 1516, 1431, 1292, 1170, 1001, 839, 721 and 547 cm⁻¹; ¹H-NMR (300 MHz, DMSO-$d_6$): d 12.80 (s, 2H), 9.10 (d, J=6.09 Hz, 4H), 8.45 (s, 2H), 8.24 (d, J=6.48 Hz, 4H), 4.59 (t, J=7.05 Hz, 4H), 2.00–1.80 (m, 4H) and 1.38–1.18 (m, 10H); ¹³C-NMR (75.46 MHz, DMSO-$d_6$): d 148.3, 145.1, 144.9, 124.0, 60.2, 30.5, 28.5, 28.2 and 25.3; MS (ESI) m/z: 451 (M–Br⁻), 449 (M–Br⁻). HRMS found for $C_{21}H_{30}BrN_4O_2$: 451.1548, 449.1567, calculated for $C_{21}H_{30}BrN_4O_2$: 451.1534, 449.1152.

Example 5

1,6-Hexylene-bis-N,N'-3-pyridiniumaldoxime dibromide (FIG. 3, 2a).

Using a procedure similar to that described in Example 1, except replacing the 1,7-dibromoheptane used therein, with 1,6-dibromohexane, and replacing the 3-pyridinealdoxime used therein with 3-pyridinealdoxime, the title compound was prepared; Yield: 82%; m.p. 242.2–243.7 (dec.); IR (KBr): 3448, 3027, 2710, 1632, 1527, 1423, 1298, 1155, 993, 945, 806, 735 and 577 cm⁻¹; ¹H-NMR (300 MHz, DMSO-$d_6$): δ12.22 (s, 2H), 9.43 (s, 2H), 9.21 (d, J=5.94 Hz, 2H), 8.76 (d, J=8.16 Hz, 2H), 8.39 (s, 2H), 8.20 (d-d, J=6.27 Hz, 7.89 Hz, 2H), 4.70 (t, J=7.38 Hz, 4H), 2.08–1.88 (m, 4H) and 1.48–1.28 (m, 4H); ¹³C-NMR (75.46 MHz, DMSO-$d_6$): δ144.4, 143.2, 142.5, 141.2, 133.4, 128.0, 60.7, 30.1 and 24.6; MS (ESI) m/z: 409 (M–Br⁻), 407 (M–Br⁻). HRMS found for $C_{18}H_{24}BrN_4O_2$: 409.1075, 407.1100, calculated for $C_{18}H_{24}BrN_4O_2$: 409.1064, 407.1082.

Example 6

1,7-Heptylene-bis-N,N'-3-pyridiniumaldoxime dibromide (FIG. 3, 2b).

Using a procedure similar to that described in Example 1, except replacing the 3-pyridinealdoxime used therein with 3-pyridinealdoxime, the title compound was prepared; Yield: 82%; m.p. 229.8–231.0 (dec.); IR (KBr): 3483, 3160, 3014, 2859, 2710, 1634, 1462, 1421, 1292, 1161, 989, 819, 740 and 680 cm⁻¹; ¹H-NMR (300 MHz, DMSO-$d_6$): δ12.24 (s, 2H), 9.42 (s, 2H), 9.19 (d, J=5.85 Hz, 2H), 8.76 (d, J=8.16 Hz, 2H), 8.39 (s, 2H), 8.19 (d-d, J=6.24 Hz, J=7.98 Hz, 2H), 4.69 (t, J=7.26 Hz, 4H), 2.06–1.86 (m, 4H) and 1.44–1.24 (m, 6H); ¹³C-NMR (75.46 MHz, DMSO-$d_6$): δ144.4, 143.2, 142.5, 141.2, 133.4, 128.0, 60.8, 30.4, 27.6 and 25.0; MS (ESI) m/z: 423 (M–Br⁻), 421 (M–Br⁻). HRMS found for $C_{19}H_{26}BrN_4O_2$: 423.1229, 421.1235, calculated for $C_{19}H_{26}BrN_4O_2$: 423.1221, 421.1239.

Example 7

1,8-Octylene-bis-N,N'-3-pyridiniumaldoxime dibromide (FIG. 3, 2c).

Using a procedure similar to that described in Example 1, except replacing the 1,7-dibromoheptane used therein, with 1,8-dibromooctane, and replacing the 3-pyridinealdoxime used therein with 3-pyridinealdoxime, the title compound was prepared; Yield: 80%; m.p. 235.2–236.5 (dec.); IR (KBr): 3464, 3113, 2937, 2704, 1633, 1502, 1427, 1292, 1153, 995, 933, 825, 682 and 557 cm⁻¹; ¹H-NMR (300 MHz, DMSO-$d_6$): δ12.24 (s, 2H), 9.40 (s, 2H), 9.18 (d, J=6.03 Hz, 2H), 8.76 (d, J=8.16 Hz, 2H), 8.39 (s, 2H), 8.19 (d-d, J=6.18 Hz, J=8.01 Hz, 2H), 4.68 (t, J=7.26 Hz, 4H), 2.05–1.85 (m, 4H) and 1.41–1.21 (m, 8H); ¹³C-NMR (75.46 MHz, DMSO-$d_6$): δ144.4, 143.2, 142.5, 141.3, 133.4, 128.0, 60.9, 30.5, 28.1 and 25.2; MS (ESI) m/z: 437 (M–Br⁻), 435 (M–Br⁻). HRMS found for $C_{20}H_{28}BrN_4O_2$: 437.1382, 435.1417, calculated for $C_{20}H_{28}BrN_4O_2$: 437.1378, 435.1395.

Example 8

1,9-Nonylene-bis-N,N'-3-pyridiniumaldoxime dibromide (FIG. 3, 2d).

Using a procedure similar to that described in Example 1, except replacing the 1,7-dibromoheptane used therein, with 1,9-dibromononane, and replacing the 3-pyridinealdoxime used therein with 3-pyridinealdoxime, the title compound was prepared; Yield: 70%; m.p. 194.5–196.3 (dec.); IR (KBr): 3396, 3038, 2717, 1632, 1503, 1429, 1296, 1149, 999, 932, 822, 727 and 681 cm⁻¹; ¹H-NMR (300 MHz, DMSO-$d_6$): δ12.17 (s, 2H), 9.38 (s, 2H), 9.16 (d, J=5.91 Hz, 2H), 8.73 (d, J=8.16 Hz, 2H), 8.36 (s, 2H), 8.17 (d-d, J=6.12 Hz, J=8.04Hz, 2H), 4.66 (t, J=7.41 Hz, 4H), 2.02–1.82 (m, 4H) and 1.37–1.17 (m, 10H); ¹³C-NMR (75.46 MHz, DMSO-$d_6$): δ144.4, 143.2, 142.5, 141.2, 133.4, 128.0, 60.9, 30.5, 28.4, 28.2 and 25.3; MS (ESI) m/z: 451 (M–Br⁻), 449 (M–Br⁻). HRMS found for $C_{21}H_{30}BrN_4O_2$: 451.1512, 449.1551, calculated for $C_{21}H_{30}BrN_4O_2$: 451.1534, 449.1552.

Example 9

1,7-Heptylene-bis-N,N'-2-pyridiniumaldoxime dichloride (FIG. 3, 3b).

Heptane 1,7-bistriflate (2.7 g, 6.81 mmol) in $CH_3NO_2$ (10 ml) was added to a solution of 2-pyridinealdoxime (2.0 g, 16.3 mmol) in $CH_3NO_2$ (30 ml) at 0° C. under nitrogen with stirring. The resulting solution was stirred at room temperature for 2 hours. Solvent was removed under reduced pressure. The residue was added to water (100 ml) and washed with ethyl acetate (3×50 ml). The aqueous solution was subjected to ion-exchange chromatography using Dowex (Cl⁻). The resulting solution was lyophilized to give the desired product 2.3 g; yield 81%; IR (KBr): 3394, 3045, 1624, 1587, 1510, 1442, 1312, 1155, 966 and 775 cm$^{-1}$; $^1$H-NMR (300 MHz, DMSO-d$_6$): d 12.30 (s, 2H), 8.14 (d, J=7.18 Hz, 2H), 7.68 (s, 2H), 7.46 (t, J=7.92 Hz, 2H), 7.26 (d, J=7.89 Hz, 2H), 7.05–6.95 (m, 2H), 3.69 (t, J=7.56 Hz, 4H), 0.76–0.56 (m, 4H) and 0.30–0.10 (m, 6H); $^{13}$C-NMR (75.46 MHz DMSO-d$_6$): d 146.8, 146.0, 145.1, 141.2, 127.3, 125.9, 57.7, 30.2, 27.7 and 25.0; MS (ESI) m/z: 341 (M-2Cl⁻—H⁺). HRMS found for C$_{19}$H$_{25}$N$_4$O$_2$: 341.1993, calculated for C$_{19}$H$_{25}$N$_4$O$_2$: 341.1977.

The intermediate heptane 1,7-bistriflate was prepared from 1,7-heptanediol using a procedure similar to that described in M.F. Salomon, *J. Am. Chem. Soc.*, 1979, 101, 4290–4299.

Example 10

1,6-Hexylene-bis-N,N'-2-pyridinium aldoxime dichloride (FIG. 3, 3a).

Using a procedure similar to that described in Example 9, except replacing the 1,7-heptanediol used therein, with 1,6-hexanediol, the title compound was prepared; yield: 85%; IR (KBr): 3383, 3095, 1626, 1578, 1491, 1439, 1327, 1161, 1024 and 775 cm$^{-1}$; $^1$H-NMR (300 MHz, DMSO-d$_6$): d 12.47 (s, 2H), 8.36 (d, J=5.97 Hz, 2H), 7.94 (s, 2H), 7.71 (t, J=7.65 Hz, 2H), 7.53 (d, J=8.94 Hz, 2H), 7.25 (t, J=7.44 Hz, 2H), 3.93 (t, J=7.26 Hz, 4H), 1.04–0.84 (m, 4H) and 0.63–0.43(m, 4H); $^{13}$C-NMR (75.46 MHz, DMSO-d$_6$): d 147.0, 146.0, 145.0, 141.2, 127.1, 125.7, 57.5, 29.9 and 24.6; MS (ESI) m/z: 327 (M-2Cl⁻—H⁺). HRMS found for C$_{18}$H$_{23}$N$_4$O$_2$: 327.1805, calculated for C$_{18}$H$_{23}$N$_4$O$_2$: 327.1824.

Example 11

1,8-Octylene-bis-N,N'-2-pyridiniumaldoxime dichloride (FIG. 3, 3c).

Using a procedure similar to that described in Example 9, except replacing the 1,7-heptanediol used therein, with 1,8-octanediol, the title compound was prepared; Yield: 83%; IR (KBr): 3447, 3086, 1626, 1508, 1489, 1329, 1163 and 1028 cm$^{-1}$; $^1$H-NMR (300 MHz, DMSO-d$_6$): d 12.26 (s, 2H), 8.10 (d, J=6.09 Hz, 2H), 7.60 (s, 2H), 7.39 (t, J=7.95 Hz, 2H), 7.18 (d, J=8.01 Hz, 2H), 6.93 (t, J=7.14 Hz, 2H), 3.63 (t, J=7.26 Hz, 4H), 0.68–0.48 (m, 4H) and 0.18–0 (m, 8H); $^{13}$C-NMR (75.46 MHz, DMSO-d$_6$): d 146.8, 146.1, 145.2, 141.2, 127.3, 125.8, 57.7, 30.2, 28.0 and 25.1; MS (ESI) m/z: 355 (M-2Cl⁻—H⁺). HRMS found for C$_{20}$H$_{27}$N$_4$O$_2$: 355.2150, calculated for C$_{20}$H$_{27}$N$_4$O$_2$: 355.2134.

Example 12

1,9-Nonylene-bis-N,N'-2-pyridiniumaldoxime dichloride (FIG. 3, 1d).

Using a procedure similar to that described in Example 9, except replacing the 1,7-heptanediol used therein, with 1,9-nonanediol, the title compound was prepared; yield: 80%; IR (KBr): 3474, 3070, 1628, 1574, 1512, 1431, 1313, 1288, 1155, 1001 and 750 cm$^{-1}$; $^1$H-NMR (300 MHz, DMSO-d$_6$): d 12.45 (s, 2H), 8.32 (d, J=6.11 Hz, 2H), 7.90 (s, 2H), 7.68 (t, J=7.88 Hz, 2H), 7.49 (d, J=7.83 Hz, 2H), 7.22 (t, J=6.65 Hz, 2H), 3.89 (t, J=6.96 Hz, 4H), 0.99–0.79 (m, 4H) and 0.49–0.29 (m, 10H); $^{13}$C-NMR (75.46 MHz, DMSO-d$_6$): d 146.8, 146.1, 145.1, 141.2, 127.3, 125.8, 57.7, 30.3, 28.4, 28.2 and 25.2; MS (ESI) m/z: 369 (M-2Cl⁻—H⁺). HRMS found for C$_{21}$H$_{29}$N$_4$O$_2$: 369.2302, calculated for C$_{21}$H$_{29}$N$_4$O$_2$: 369.2302.

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A compound of formula I:

$$Ar^1\!-\!R^1\!-\!Ar^2 \qquad (I)$$

wherein
Ar$^1$ and Ar$^2$ are each 2-hydroxyiminomethyl-1-pyridyl, attached to R$^1$ via a ring nitrogen; and
R$^1$ is an unbranched (C$_7$)-, (C$_8$)-, or (C$_9$)alkylene chain, optionally substituted with one, two, or three substituents selected from the group consisting of (C$_1$–C$_3$) alkoxy, hydroxy, and halo; or
R$^1$ is an unbranched (C$_2$–C$_{10}$)alkylene chain comprising at least one divalent radicals selected from the group consisting of —OC(=O)—, —NHC(=O)—, —NHC(=O)C(=O)NH—, —OCH$_2$C=CCH$_2$O—, 1,4-phenylene, 1,3-phenylene, 1,2-phenylene, 1,4-cyclohexadiyl, 1,3cyclohexadiyl, and 1,3-cyclopentadiyl; or a pharmaceutically acceptable salt thereof.

2. The compound of claim 1 wherein R$^1$ is an unbranched (C$_7$)-, (C$_8$)-, or (C$_9$)alkylene chain, optionally substituted with one, two, or three substituents selected from the group consisting of (C$_1$–C$_3$)alkoxy, hydroxy, and halo.

3. The compound of claim 1 wherein R$^1$ is an unbranched (C$_2$–C$_{10}$)alkylene chain comprising within said chain a divalent radical selected from the group consisting of —OC(=O)—, —NHC(=O)—, —NHC(=O)C(=O)NH—, and —OCH$_2$C=CCH$_2$O—.

4. The compound of claim 1 wherein R$^1$ is an unbranched (C$_2$)-, (C$_3$)-, (C$_4$)-, or (C$_5$)-alkylene chain comprising within said chain a divalent radical selected from the group consisting of 1,4-phenylene, 1,3-phenylene, 1,2-phenylene, 1,4-cyclohexadiyl, 1,3cyclohexadiyl, and 1,3-cyclopentadiyl.

5. The compound of claim 1 wherein R$^1$ is 1,7-heptadiyl, 1,8-octadiyl, or 1,9-nonadiyl.

6. The compound of claim 1 wherein R$^1$ is an unbranched (C$_7$)alkylene chain, optionally substituted with one, two or three substituents selected from the group consisting of (C$_1$–C$_3$)alkoxy, hydroxy, oxo, and halo.

7. The compound of claim 1 wherein R$^1$ is an unbranched (C$_6$)-, (C$_7$)-, (C$_8$)-, (C$_9$)-, or (C$_{10}$)-alkylene chain comprising within said chain a divalent radical —OC(=O)— or —NHC(=O)—.

8. The compound of claim 1 wherein R$^1$ is an unbranched (C$_2$)-, (C$_3$)-, (C$_4$)-, or (C$_5$)-alkylene chain comprising within said chain a divalent radical —NHC(=O)C(=O) NH— or —OCH$_2$C=CCH$_2$O—.

9. The compound of claim 1 wherein R$^1$ is 1,7-heptadiyl.

10. The compound of claim 1 which is 1,7-heptylene-bis-N,N'-2pyridiniumaldoxime dichloride.

11. The compound of claim 1, wherein R$^1$ has a chain length of approximately 14–20 Å.

12. The compound of claim 1, wherein R$^1$ has a chain length of approximately 16–18 Å.

13. A pharmaceutical composition comprising a compound of claim 1; or a pharmaceutically acceptable salt thereof; and a pharmaceutically acceptable diluent or carrier.

14. A method comprising attenuating the effects on a mammal caused by exposure to a chemical agent that covalently inhibits AChE, by administering to said mammal an effective amount of a compound of claim 1.

15. The method of claim 14 wherein said compound is administered prior to exposure to said chemical agent.

16. The method of claim 14 wherein said compound is administered after exposure to said chemical agent.

17. The method of claim 14 further comprising administering atropine to said mammal.

18. The method of claim 14 further comprising administering to said mammal an antimuscarinic and/or an antinicotinic agent.

19. The method of claim 14 wherein the mammal is a human.

* * * * *

UNITED STATES PATENT AND TRADEMARK OFFICE
CERTIFICATE OF CORRECTION

PATENT NO.: 5,929,093

DATED: 7/27/99

INVENTOR(S): Pang et al.

It is certified that errors appear in the above-identified patent and that said Letters Patent is hereby corrected as shown below:

In column 12, line 24, delete "=CCH$_{20}$O" and insert -- =CCH$_2$O--, therefore.
In column 12, line 26, after ",3", insert "-", first occurance.
In column 12, line 42, after ",3", insert "-", first occurance.

Signed and Sealed this

Twenty-fifth Day of April, 2000

Attest:

Q. TODD DICKINSON

*Attesting Officer*        *Director of Patents and Trademarks*